United States Patent [19]

Enger

[11] Patent Number: 5,728,067
[45] Date of Patent: Mar. 17, 1998

[54] RAPIDLY EXCHANGEABLE CORONARY CATHETER

[75] Inventor: Christine D. Enger, Tenafly, N.J.

[73] Assignee: C. R. Bard, Inc., Murray Hill, N.J.

[21] Appl. No.: 642,334

[22] Filed: May 3, 1996

Related U.S. Application Data

[60] Continuation of Ser. No. 477,617, Jun. 7, 1995, abandoned, which is a division of Ser. No. 95,036, Jul. 20, 1993, which is a continuation-in-part of Ser. No. 999,589, Dec. 30, 1992, abandoned, which is a continuation-in-part of Ser. No. 759,107, Sep. 6, 1991, abandoned, which is a continuation-in-part of Ser. No. 618,531, Nov. 26, 1990, abandoned, which is a continuation-in-part of Ser. No. 303,803, Jan. 30, 1989, abandoned.

[51] Int. Cl.$^6$ ............................................. A61M 29/00
[52] U.S. Cl. ............................. 604/102; 604/96; 606/194
[58] Field of Search .............................. 604/96–103, 170, 604/282; 606/192–196; 600/18

[56] References Cited

U.S. PATENT DOCUMENTS

| 871,474 | 11/1907 | Buckner . |
| 2,024,301 | 12/1935 | Norwood . |
| 2,930,377 | 3/1960 | Cowley . |

(List continued on next page.)

FOREIGN PATENT DOCUMENTS

| 0274129 | 7/1988 | European Pat. Off. . |
| 0397357 | 11/1990 | European Pat. Off. . |
| 2340078 | 10/1977 | France . |
| 62-116746 | 5/1987 | Japan . |
| WO8603129 | 6/1986 | WIPO . |
| WO8803422 | 5/1988 | WIPO . |

OTHER PUBLICATIONS

Werns, "Review of Hardware for PTCA", *Journal of Interventional Cardiology*, vol. 1, No. 3, 1988, pp. 209–219.

Thomas et al., "Efficacy of a New Angioplasty Catheter for Severely Narrowed Coronary Lesions", *Journal of the American College of Cardiology*, vol. 12, pp. 694–702.

Meier, "Coronary Angioplasty", 1987, pp. 13–15.

(List continued on next page.)

*Primary Examiner*—Mark Bockelman
*Assistant Examiner*—Jennifer R. Sadula
*Attorney, Agent, or Firm*—Arthur Z. Bookstein

[57] ABSTRACT

A rapidly exchangeable catheter for use in the coronary arteries includes an elongate relatively stiff proximal segment that defines an inflation lumen, an intermediate, shorter segment formed from a more flexible plastic material and having two lumens, and a third, single lumen distal segment. A balloon or other instrumentality adapted to operate in a coronary artery is mounted to the distal region of the catheter. The intermediate and distal segments include a guidewire lumen by which the catheter may be advanced along a guidewire. The proximal segment may include an inflation lumen when the operating instrumentality at the distal end of the catheter is a balloon. The intermediate and distal segments of the catheter are of a length of between about 35 to 45 cm such that when the catheter is advanced into the most remote distal portions of the coronary anatomy, the flexible plastic intermediate and distal segments will extend over the aortic arch of the patient thereby containing the guidewire over the aortic arch and maintaining the juncture of the relatively stiff proximal segment and the more flexible intermediate segment proximally of the aortic arch. The relatively stiff proximal section thus extends generally along a straight line from the femoral artery into the descending aorta but not so far as into the aortic arch. Buckling of the catheter is avoided so that the catheter is more easily manipulated.

22 Claims, 3 Drawing Sheets

U.S. PATENT DOCUMENTS

| | | |
|---|---|---|
| 3,769,981 | 11/1973 | McWhorter . |
| 4,055,682 | 10/1977 | Merrill . |
| 4,173,981 | 11/1979 | Mortensen . |
| 4,195,637 | 4/1980 | Grüntzig et al. . |
| 4,328,806 | 5/1982 | Cooper . |
| 4,402,307 | 9/1983 | Hanson et al. . |
| 4,490,421 | 12/1984 | Levy . |
| 4,545,390 | 10/1985 | Leary . |
| 4,581,017 | 4/1986 | Sahota . |
| 4,616,652 | 10/1986 | Simpson . |
| 4,616,653 | 10/1986 | Samson et al. . |
| 4,652,258 | 3/1987 | Drach . |
| 4,655,748 | 4/1987 | Mushika ............................ 604/96 |
| 4,748,982 | 6/1988 | Horewski . |
| 4,762,129 | 8/1988 | Bonzel . |
| 4,771,777 | 9/1988 | Horzewski et al. ............. 604/102 X |
| 4,775,371 | 10/1988 | Mueller, Jr. . |
| 4,798,193 | 1/1989 | Giesy et al. . |
| 4,813,930 | 3/1989 | Elliott . |
| 4,820,271 | 4/1989 | Deutsch . |
| 4,824,435 | 4/1989 | Giesy et al. . |
| 4,827,941 | 5/1989 | Taylor et al. . |
| 4,827,999 | 5/1989 | Yabuki et al. . |
| 4,846,174 | 7/1989 | Willard et al. ..................... 604/96 X |
| 4,877,031 | 10/1989 | Conway et al. .................... 604/96 X |
| 4,892,519 | 1/1990 | Songer et al. . |
| 4,943,278 | 7/1990 | Euteneuer et al. . |
| 4,988,356 | 1/1991 | Crittenden . |
| 4,998,917 | 3/1991 | Gaiser et al. . |
| 4,998,923 | 3/1991 | Samson et al. . |
| 5,024,234 | 6/1991 | Leary et al. . |
| 5,040,548 | 8/1991 | Yock . |
| 5,046,503 | 9/1991 | Schneiderman . |
| 5,061,273 | 10/1991 | Yock . |
| 5,102,403 | 4/1992 | Alt . |

OTHER PUBLICATIONS

Myler et al., "The Balloon on a Wire Device: A New Ultra–Low–Profile Coronary Angioplasty System/Concept", *Catheterisation and Cardiovascular Diagnosis*, vol. 14, 1988, pp. 135–140.

Brochure for Bard "Probe" PTCA Dilatation System, 1987.

Brochure for SciMed "Ace" fixed–wire PTCA catheter, Dec. 1988.

Catalogue for Schneider–Shiley Monorail Bonzel Coronary Diltation System, Oct. 1988.

Brochure for Schneider Monorail™–Piccolino catheter, Oct. 1988.

Finci et al., "Clinical Experience with the Monorail Balloon Catheter for Coronary Angioplasty", *Catheterisation and Cardiovascular Diagnosis*, vol. 14, 1988 pp. 206–212.

Brochure for ACS Hartzler™LPS® Dilatation catheter, 1985.

RAPIDLY EXCHANGEABLE CORONARY CATHETER

This application is a continuation of application Ser. No. 08/477,617 filed Jun. 7, 1995, now abandoned, which is a divisional of application Ser. No. 08/095,036 filed Jul. 20, 1993 pending, which is a continuation of application Ser. No. 07/999,589 filed Dec. 30, 1992, now abandoned, which is a continuation of application Ser. No. 07/759,107 filed Sep. 6, 1991, now abandoned, which is a continuation of application Ser. No. 07/618,531 filed Nov. 26, 1990, now abandoned, which is a continuation of application Ser. No. 07/303,803 filed Jan. 30, 1989, now abandoned.

FIELD OF THE INVENTION

This invention relates to balloon dilatation catheters and particularly to such catheters as are used in percutaneous transluminal coronary angioplasty.

BACKGROUND OF THE INVENTION

Dilatation catheters, and particularly, those used for percutaneous transluminal coronary angioplasty (PTCA), typically include an elongate flexible shaft of the order of 150 cm long having a dilatation balloon mounted to the distal end of the shaft and an inflation lumen extending longitudinally within the shaft from its proximal end to the interior of the balloon so that the balloon may be inflated and deflated. Typically, such PTCA catheters also are provided with a full length guidewire lumen that is open at the distal tip of the shaft at a distal outlet opening. The proximal end of the guidewire lumen is open at the proximal end of the catheter. The guidewire lumen receives a guidewire which, when the guidewire and catheter are placed within a patient's artery, can be manipulated to guide the wire and catheter to the desired branch of the patient's arteries.

Typically, the balloon dilatation catheter and guidewire are guided to the entrance to the coronary arteries by a previously placed guide catheter. The guide catheter commonly is percutaneously inserted into the patient's femoral artery and is advanced along the aorta toward the heart. The guide catheter typically is provided with a preshaped distal tip adapted to remain at the coronary ostium leading to the coronary artery. Once placed, the guide catheter provides direct, quick access to the entrance to the coronary arteries.

It is common during a PTCA procedure for the physician to exchange the balloon catheter for another catheter, for example, if it is desired to change balloon sizes. This may occur, for example, if the physician initially performed a partial dilatation with a small diameter balloon and then wished to further dilate the patient's artery by using a catheter having a larger balloon. Such a catheter exchange may be accomplished in several ways. In one technique, the conventional guidewire which may be approximately 175 cm long is removed from the in situ balloon catheter and is replaced with a longer exchange wire, typically about 300 cm long. The length of the exchange wire that extends out of the patient is greater than the length of the balloon catheter thus providing a means by which the guidewire may be grasped at all times to prevent inadvertent withdrawal of the guidewire as the catheter is withdrawn. Once the catheter is withdrawn over the exchange wire, the next catheter can be threaded over the exchange wire and inserted into the patient, the exchange wire providing a direct path to guide the catheter to the portion of the artery to be dilated. If desired, the exchange wire then may be removed and replaced with a shorter conventional wire, although some physicians may prefer to permit the exchange wire to remain in place for the remainder of the procedure.

Another technique omits the necessity for an exchange wire by providing a guidewire extension that is attached to the proximal end of the guidewire thereby effectively extending the length of the guidewire that protrudes out of a patient sufficiently to permit the catheter to be withdrawn and a new catheter to be threaded back into the patient without losing guidewire position.

Still another technique for performing a catheter exchange is that described in "New Instruments for Catheterization and Angiocardiography" by Bjorn Nordenstrom, *Radiology*, Vol. 85, 1965, pp. 256–259, which describes a catheter having a relatively short guidewire lumen at the distal end of the catheter, the guidewire lumen having a proximal terminal opening located distally of the proximal end of the catheter shaft. In this arrangement, the guidewire passes through the catheter shaft only for a segment of the length of the shaft. The catheter can be moved along the guidewire in the fashion of a "monorail". Because the guidewire lumen is relatively short and is considerably shorter than the overall length of the catheter, the catheter can be withdrawn from the patient over the original guidewire without dragging the guidewire out of the artery together with the catheter because the length of guidewire protruding from the patient is longer than the length of the guidewire lumen of the catheter. Thus, a portion of the guidewire is exposed at all times and may be grasped by the physician. Such a monorail system has recently been incorporated into PTCA catheters as illustrated, for example, in U.S. Pat. Nos. 4,762,129 (Bonzel) and 4,748,982 (Horzewski).

Although the use of the monorail system facilitates catheter exchanges, the PTCA catheters in which the monorail system have been incorporated have presented some difficulties. One of the problems presented is that because the guidewire only extends through a relatively small portion of the overall length of the catheter, the remaining portion of the catheter shaft is unsupported by the guidewire. When the balloon catheter and guidewire are advanced through the guide catheter by pushing the catheter shaft, the unsupported portion of the catheter shaft tends to buckle within the guide catheter. Buckling of the catheter shaft within the guide catheter increases the number and area of points of contact between the catheter shaft and the inner surface of the guide catheter lumen, thus increasing friction and causing the balloon catheter to bind up in the guide catheter and impairing the ability of the catheter to be pushed along the guidewire. The tendency to become bound up in the guide catheter increases with the extent to which the catheter is advanced through the guide catheter and prevents the catheter from being advanced into distal coronary vasculature. The tendency for the dilatation catheter shaft to buckle is particularly acute in the region of the aortic arch.

It is among the general objects of the invention to provide an improved PTCA catheter having a rapid exchange feature which avoids the foregoing and other difficulties.

SUMMARY OF THE INVENTION

The catheter of the present invention is formed from a composite shaft that includes an elongate proximal segment formed from a relatively stiff metal tube and defining an inflation lumen, an intermediate, shorter segment formed from a more flexible, plastic material and having two lumens, and a third single lumen distal segment. The intermediate segment includes an inflation lumen that is a continuation of the inflation lumen of the proximal segment and a second, parallel guidewire lumen. The third, distal tubular segment is formed from flexible plastic material and has a single lumen which is a continuation of the guidewire lumen in the intermediate segment and opens at a distal outlet tip. The dilatation balloon is mounted on the distal end of the catheter with its proximal end mounted to the intermediate segment and its distal end mounted to the distal segment. The guidewire lumen has a proximal opening proximally of the balloon and communicates with the lumen of the distal segment and distal outlet opening distally of the balloon.

The intermediate and distal segments are of a combined length, between about 35 cm to 45 cm, such that with the catheter advanced into the most remote distal portions of the coronary anatomy, the flexible plastic intermediate segment will extend over the aortic arch of the patient. The juncture of the relatively stiff proximal segment and the more flexible-intermediate segment thus remains proximally of the aortic arch so that the relatively stiff elongate proximal section extends generally along a straight line from the femoral artery into the descending aorta, but not so far as into the aortic arch. The moderately flexible proximal segment is sufficiently stiff and is self-supporting so that it will not buckle in the guide catheter as the catheter is pushed in a distal direction. Additionally, the intermediate and distal segments of the catheter are fully supported by the guidewire that extends through the guidewire lumen and thereby provides substantial support for the intermediate and distal segments of the catheter. The catheter construction does not tend to bind up within the guide catheter and thereby facilitates advancement of the distal balloon end of the catheter into more distal regions of a patient's coronary anatomy. Moreover, because the cross-section of the metal tubular proximal segment is relatively small, it presents reduced obstruction through the guide catheter to a flow of radiopaque contrast liquid and, thereby, makes it easier for the physician to inject contrast liquid into the patient's coronary arteries in order to visualize them fluoroscopically.

It is among the general objects of the invention to provide an improved rapidly exchangeable balloon dilatation catheter.

Another object of the invention is to provide a rapidly exchangeable balloon dilatation catheter which is provided with axial support along the full length of the catheter.

Another object of the invention is to provide a rapidly exchangeable catheter having a relatively flexible distal portion that receives a guidewire and is of sufficient length that it can extend from the distal coronary anatomy over the aortic arch and into the descending aorta.

A further object of the invention is to provide a rapidly exchangeable catheter having an elongate moderately flexible self-supporting proximal section and at least one distal section that is more flexible and has a guidewire lumen extending therethrough whereby the guidewire may support said distal segments.

A further object of the invention is to provide a rapidly exchangeable catheter which has a reduced tendency to buckle within the guide catheter.

Another object of the invention is to provide a rapidly exchangeable catheter which provides reduced friction in the guide catheter.

A further object of the invention is to provide a rapidly exchangeable catheter which better enables the physician to advance the distal end of the catheter into the distal coronary anatomy of a patient.

DESCRIPTION OF THE DRAWINGS

The foregoing and other objects and advantages of the invention will be appreciated more fully from the following further description thereof, with reference to the accompanying drawings wherein.

DESCRIPTION OF THE ILLUSTRATIVE EMBODIMENT

Figure 3:
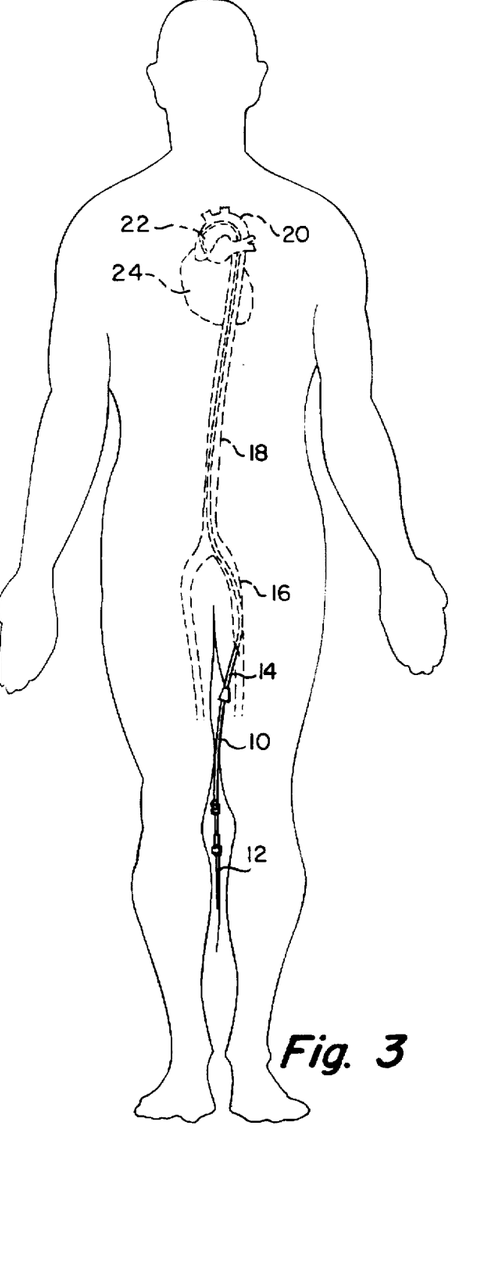
FIG. 3 is a diagrammatic illustration of a patient showing the manner in which a balloon catheter is advanced from the femoral artery through the aorta to the patient's heart.

FIG. 3 illustrates, diagrammatically, a conventional over-the-wire balloon dilatation catheter 10 and a guidewire 12 inserted into the patient's vasculature through a guide catheter 14. The guide catheter 14 is initially placed, percutaneously, into the patient's femoral artery 16 and is advanced along the descending aorta 18 over the aortic arch 20 and into the ascending aorta 22 that leads from the heart 24. As will be appreciated by those skilled in the art, the distal end of the guide catheter is specially shaped so that the distal tip 23 of the guide catheter will easily lodge in the entrance to the right 25 or left 27 coronary artery (see FIG. 4).

When it is desired to exchange the balloon catheter 10 for another, it is important that the guidewire 12 be maintained within the patient's artery so that it may guide the next succeeding catheter quickly and efficiently to the intended site in the patient's vascular system. Typically, the clearances between the guidewire 12 and the inner lumen of the catheter 10, coupled with the bends which the catheter 10 and guidewire 12 must follow along the patient's artery are such that withdrawal of the catheter 10 tends to drag the guidewire 12 out with the catheter 10. In order to maintain the guidewire 12 in place while the catheter 10 is withdrawn, it is necessary to hold the guidewire 12 by its proximal end while withdrawing the catheter 10 over the guidewire 12.

Among the techniques for facilitating a catheter exchange is the use of a monorail-type of catheter in which the guidewire lumen in the catheter extends only over a relatively short length of the catheter at the distal end of the catheter. Because the guidewire lumen is shorter than the portion of the guidewire that protrudes out of the patient, some part of the guidewire is always exposed and may be grasped to maintain guidewire position. With the monorail system, it is unnecessary to use exchange wires or other devices to increase the effective length of the guidewire in order to perform a catheter exchange.

Figure 1:
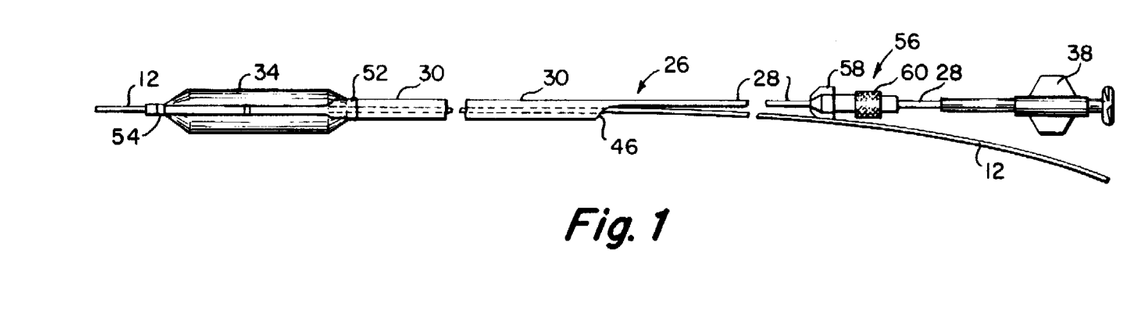
FIG. 1 is a fragmented illustration of the catheter.
Figure 2:
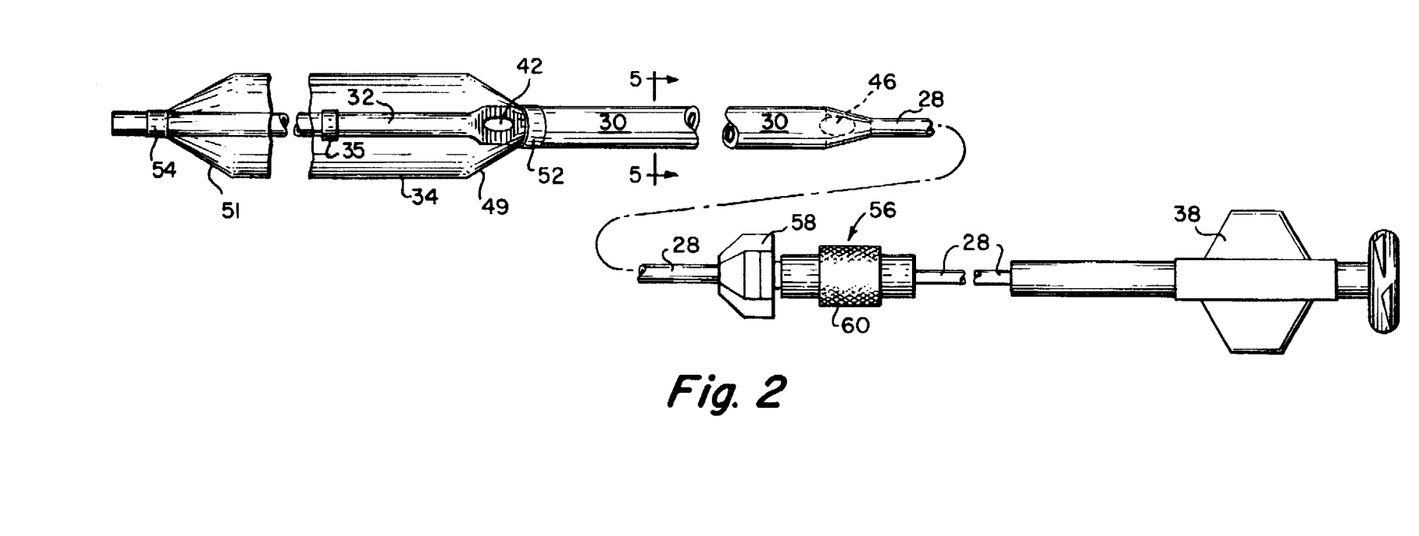
FIG. 2 is an enlarged illustration of the catheter.
Figure 7:
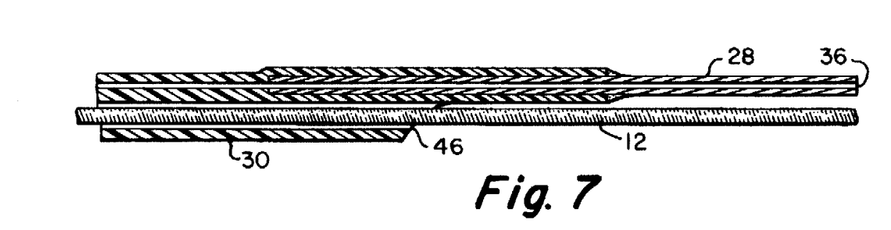
FIG. 7 is a sectional longitudinal illustration of the catheter in the region where the proximal metal tubular segment is joined to the intermediate more flexible plastic segment.

FIG. 2 is a fragmented illustration of a catheter in accordance with the invention. The catheter 26 includes an elongate proximal segment 28 which is formed from metallic hypodermic tubing, preferably stainless steel. The proximal segment may be of the order of 100 to 110 cm long. The tubing 28 may be of the order of 0.022" outer diameter with a wall thickness of about 0.003". The catheter 26 also includes an intermediate segment 30 attached at its proximal end to the distal end of the metal tube 28 and being shorter in length than the metal tube 28. The catheter also includes a distal segment 32 (FIGS. 2 and 8) attached to the distal end of the intermediate segment 30. A dilatation balloon 34 is mounted on the distal segment 32 as will be described. The metallic tubular proximal segment 28 defines a lumen 36 (FIG. 7) that extends fully through its length. A luer fitting 38 is attached to the proximal end of the tubing 28 to connect the lumen 36 with an inflation/deflation device, such as a syringe (not shown). The lumen 36 communicates with a lumen 40 (FIG. 8) in the intermediate segment 30. The lumen 40 terminates at a port 42 disposed within the balloon 34. Thus, the balloon 34 may be inflated and deflated through the inflation/deflation lumens 36, 40 in the metal tube 28 and intermediate segment 30, respectively.

As will be described, the metal tubular segment 28 provides for a high degree of column strength and enables the catheter to be pushed from its proximal end without buckling. The metal tube 28 may be coated with a thin film of lubricious material, such as Teflon, polytetrafluoroethylene.

Figure 5:
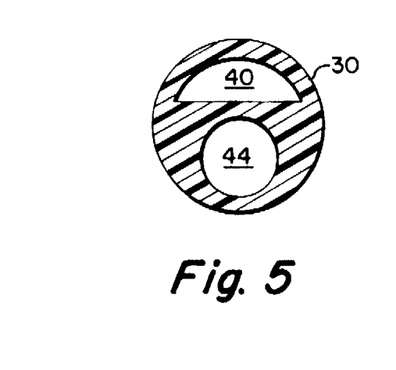
FIG. 5 is a cross-sectional illustration of the two lumen segment of the intermediate segment of the catheter as seen along the line 5—5 of FIG. 2.

The flexible plastic intermediate segment 30 may be an extruded tube of suitable plastic such as high density polyethylene. The intermediate segment 30 may be of the order of 0.045 inches outer diameter. The length of the intermediate segment 30 is between about 30 to 40 cm for reasons discussed below. The intermediate segment 30 has two lumens including the inflation lumen 40 which may be somewhat D-shaped as illustrated in FIG. 5. The other lumen 44 may be circular as shown in FIG. 5 and is adapted to receive the guidewire 12. The guidewire lumen 44 may be of the order of 0.020 inches diameter. The guidewire lumen terminates in a proximal opening 46 so that the guidewire is exposed proximally of the intermediate segment 30. Thus, the guidewire may extend within the guide catheter 14 in parallel to and outside of the proximal segment 28.

Figure 6:
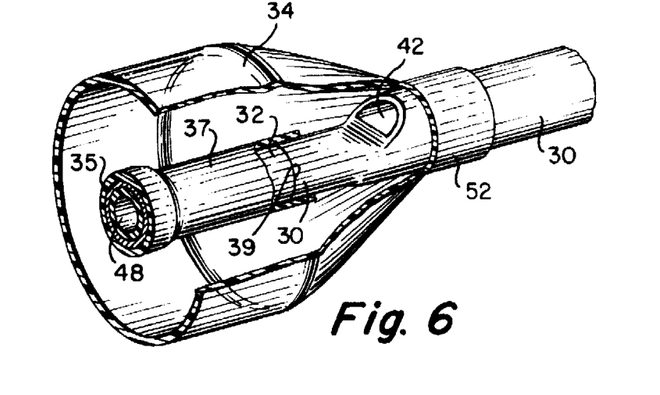
FIG. 6 is an enlarged illustration of the proximal end of the balloon and its point of attachment to the intermediate segment.

The distal segment 32 of the catheter is formed from a separate length of single lumen tubing which may be extruded from a relatively flexible plastic material such as low density polyethylene. The distal segment 32 is circular in cross-section and has a circular lumen 48 FIG. 6 which is an extension of the guidewire lumen 44 in the intermediate segment 30. The distal tip of the distal segment 32 is open at a distal outlet orifice 33 FIG. 8. The distal segment 32 may be attached by fusing its proximal end to the distal end of the intermediate segment 30 while maintaining continuation of the guidewire lumen 44, 48 and the opening 42 of the inflation lumen 40 by inserting mandrels in those lumens during the fusion process. A highly radiopaque marker band 35 preferably is mounted on the distal segment 32 and is encapsulated in an overlying thin polyethylene sleeve 37, the sleeve 37 extending proximally over the joint 39 between the intermediate segment 30 and distal segment 32. The sleeve 37 also is heat fused to the shaft. The distal segment 32 may have a wall thickness of the order of 0.0035 inches thereby making it more flexible than the more massive intermediate segment 30. The radiopaque marker band 35 can be formed from an appropriate radiopaque material such as gold or platinum.

Figure 8:
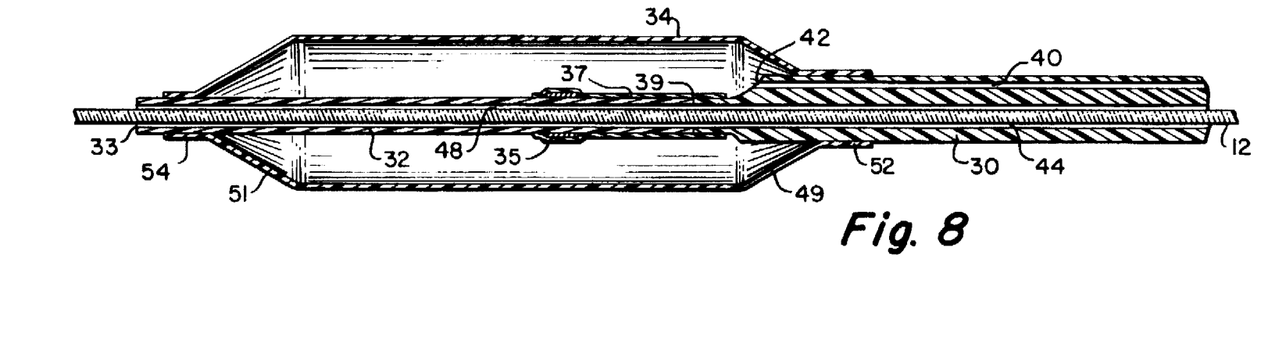
FIG. 8 is an enlarged longitudinal sectional illustration of the distal end of the catheter showing the balloon and the manner of its attachment to the intermediate and distal segments.

The balloon 34 is mounted on the distal region of the catheter. The balloon 34 may be formed from a suitably flexible strong and relatively inelastic material such as polyethylene terephthalate. The balloon may be formed in a procedure described in U.S. Pat. No. 4,490,421 to Levy. The balloon may be of the order of 20 mm long and may have a balloon diameter when inflated of from about 1.5 mm to 4.0 mm. The wall thickness may be of the order of 0.0005" to 0.001". The balloon includes an elongate cylindrical portion having integral tapering conical sections 49, 51 at each of its proximal and distal ends. Each of the conical sections merges into a small diameter cylindrical neck, the neck 52 at the proximal end of the balloon being larger in diameter than the neck 54 at the distal end. The proximal neck 52 is mounted on the distal region of the intermediate segment 30 and the distal neck 54 is mounted on the distal portion of the distal segment 32. The neck portions 52, 54 are securely bonded to the intermediate and distal segments 30, 32, respectively, by an appropriate adhesive such as an epoxy.

Figure 4:
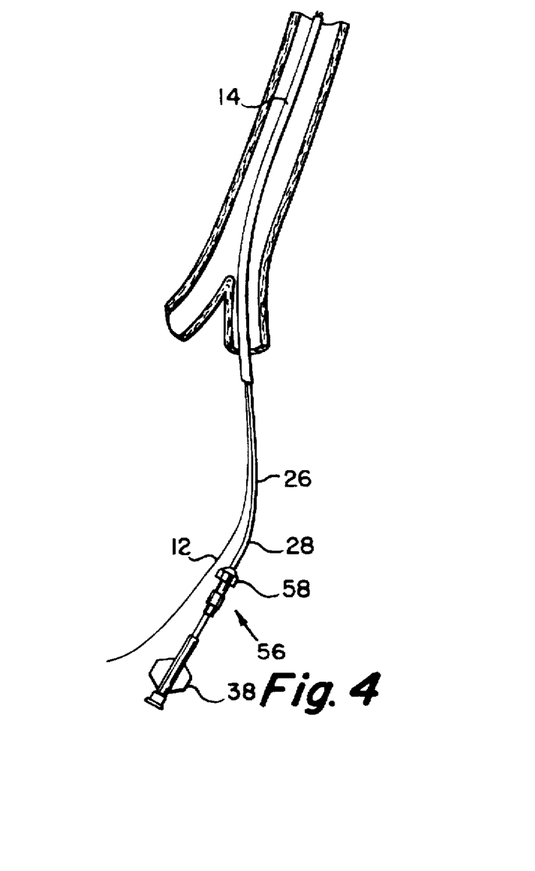
FIG. 4 is an illustration of the aorta leading from the heart and coronary arteries with a guide catheter in place and the catheter of the present invention extending through the guide catheter.

The manner in which the catheter of the present invention is used will be appreciated from FIGS. 3 and 4. In a typical procedure, the femoral artery 16 is accessed percutaneously by a hollow needle. After inserting the needle into the femoral artery, a relatively large diameter guidewire (about 0.038" diameter) is advanced through the needle and into the femoral artery. The needle is removed and an introducer sheath and dilator are placed inside the artery. The dilator is then removed. The guide catheter is inserted over the guidewire and is advanced along with the guidewire to the ascending aorta when the 0.038" guidewire is removed. The distal end of the guide catheter 14 is shaped specially to be easily inserted into the entrance of one of the two coronary ostia to access either the right or left main coronary arteries. FIG. 4 illustrates a guide catheter 14 seated in the left coronary ostium. Once the guide catheter is in place, the 0.038" guidewire may be removed. The guide catheter 14 then is ready to receive the dilatation catheter and its small diameter (e.g., 0.010"-0.018" diameter) guidewire.

In placing the small diameter steerable guidewire 12 and the conventional over-the-wire balloon dilatation catheter 10, it is conventional practice to first assemble the guidewire 12 with the balloon catheter 10 and then pass them both in unison through the guide catheter. Alternately, with the present invention, the guidewire 12 may be inserted through the guide catheter by itself. The guidewire is advanced to the coronary ostium and then may be further advanced into the coronary arteries. The guidewire may be of the type described in U.S. Pat. No. 4,545,390 to Leary and may be steerable so that it can be manipulated and guided to the desired branch of the coronary arteries to be treated. The progress of the guidewire through the patient's coronary arteries may be monitored fluoroscopically by the physician. The physician also may inject radiopaque contrast liquid through the guide catheter to visualize the coronary anatomy on the fluoroscope. Once the guidewire 12 has been advanced through the stenosis to be treated, the balloon catheter 26 of the present invention is advanced over the guidewire 12 and within the guide catheter 14. The catheter 26 will track smoothly and easily along the guidewire with no significant tendency to buckle. This results from the relatively stiff, pushable nature of the elongate metal tubular proximal segment 28 of the catheter. Additionally, the intermediate and distal segments 30, 32 are supported by the guidewire 12 which provides significant resistance to buckling of the intermediate and distal segments 30, 32. It will be appreciated, therefore, that when the catheter 26 is advanced over the guidewire, the catheter will have significant axial, column support fully along its length. In this regard, it is important to note that the proximal end of the guidewire lumen 44 in the intermediate segment 30 overlaps longitudinally, the distal end of the metal tubular proximal segment 28 that is embedded in the proximal end of the intermediate segment 30. Thus, when the catheter is advanced over the guidewire 12, there is column support fully along the length of the catheter, from its proximal to its distal end. As a result, there is considerably reduced tendency for any portion of the catheter to buckle longitudinally. Consequently, the friction between the balloon dilatation catheter 26 and the guide catheter 14 is substantially reduced thereby enabling the distal end of the catheter to be advanced into distal, remote and tortuous regions of the patient's coronary anatomy.

In order to better grasp the proximal end of the catheter to push it through the guide catheter, a gripping device 56 may be mounted on the proximal segment 28. The gripping device 56 includes a nut 58 which is threaded into a tubular collet 60. The collet 60 and nut 58 are screwed together over the proximal segment 28 to cause the collet 60 to securely grip the proximal segment 28. The position of the gripping device 56 may be adjusted by loosening the nut and repositioning the device.

It should be noted that the length of the intermediate and distal segments 30, 32 are selected so that when the balloon is placed in a very distal region of the coronary anatomy, the juncture of the proximal end of the intermediate segment with the proximal tubular segment 28 is disposed in the descending aorta 18 and does not extend into the aortic arch 20. Thus, the combined length of the intermediate and distal segments 30, 32 should be between 35 to 45 cm long, with a length of 40 cm being preferred for most patients' anatomies. It will be appreciated from the foregoing construction that the flexible intermediate and distal portions 30, 32 will pass easily through the curve of the aortic arch 20 without tendency to buckle because they are fully supported by the guidewire 12. The relatively stiff elongate metal proximal segment 28 does not pass through the aortic arch 20 and maintains its relatively straight configuration so that its pushable characteristics are not compromised. There is minimal tendency of the catheter to dislodge the distal tip of the guide catheter from its position in the coronary ostium.

Should it be desired to exchange the balloon catheter 26 for another catheter, there is no need to use an extended length guidewire. Typically, about 50 cm of the guidewire 12 will protrude exteriorly of the patient. When the catheter 26 is withdrawn, a segment of the guidewire 12 will be exposed at all times, thereby enabling the guidewire 12 to be grasped to maintain its position in the patient. Thus, the catheter 26 may be withdrawn without dragging the guidewire 12 out of position. After the first catheter has been removed, another catheter may be threaded onto the guidewire and advanced through the guide catheter and into the coronary anatomy, guided by the guidewire 12. The catheter constructed in accordance with the invention will be advanced easily, without tendency to buckle or develop high friction within the guide catheter and with no significant tendency to dislodge the guide catheter from its position at the coronary ostium.

From the foregoing, it will be appreciated that the invention provides an improved rapidly exchangeable catheter construction and catheterization method.

It should be understood, however, that the foregoing description of the invention is intended merely to be illustrative thereof and that other modifications and embodiments may be apparent to those skilled in the art without departing from its spirit.

For example, although the invention has been illustrated in connection with a balloon dilatation catheter, it may also be incorporated in other types of catheters, such as laser catheters, hot tip catheters, infusion catheters, artherectomy catheters and the like.

Having thus described the invention, what I desire to claim and secure by letters patent is:

1. A balloon dilatation catheter for percutaneous transluminal coronary angioplasty, the catheter having a proximal end and a distal end and comprising:

an elongate stiff proximal segment, formed of hypotubing, having an inflation lumen extending therethrough;

an intermediate elongate plastic catheter segment attached to the distal end of the proximal segment, the intermediate segment being more flexible than the proximal segment and having two lumens formed therethrough including a first lumen in fluid flow communication with the inflation lumen of the proximal segment to define a continuation of the inflation lumen, the inflation lumen in the intermediate segment terminating in an outlet port, the intermediate segment having a second, guidewire lumen extending parallel to the first lumen and being adapted to receive a guidewire, the guidewire lumen having a proximal opening in the region of the juncture of the intermediate and proximal segments;

the proximal segment being smaller in diameter than the intermediate segment and being substantially stiffer than the intermediate segment, the proximal segment having sufficient column strength to resist buckling when advanced through the patient's arteries;

a distal segment attached to the distal end of the intermediate segment and defining an elongate lumen in communication with and being a continuation of the distal end of the guidewire lumen of the intermediate segment, and terminating, at its distal tip, in a distal outlet;

the guidewire lumen through the intermediate and distal segments being open only at said proximal opening and said distal outlet, the intermediate and distal segments completely and continuously circumscribing the guidewire lumen to preclude a guidewire from exiting the guidewire lumen laterally between the proximal opening and the distal outlet;

a dilatation balloon having proximal and distal ends, the proximal end of the balloon being mounted on the intermediate segment, the interior of the balloon being in communication with the outlet port of the inflation lumen;

the distal end of the proximal segment being connected to the proximal end of the intermediate segment in overlapping relation with the proximal end of the guidewire lumen including the proximal opening of the guidewire lumen, whereby when a guidewire is received in the guidewire lumen the catheter will have continuous column support fully along its length from the proximal end of the proximal segment to the distal outlet of the distal segment.

2. A balloon dilatation catheter as defined in claim 1 wherein the distal segment is of smaller diameter and is more flexible than the intermediate segment.

3. A balloon dilatation catheter as defined in any of claims 1 or 2 further comprising, in combination, a guidewire extending through the guidewire lumen.

4. A catheter as defined in any of claims 1 or 2 wherein the proximal segment is formed from a metal tube of smaller cross-sectional dimensions than the intermediate plastic segment.

5. A balloon dilatation catheter as defined in any of claims 1 or 2 wherein the distal and intermediate segments extend over a combined length of between 35 to 45 cm and wherein the overall length of the catheter is between about 145 to 155 cm.

6. A balloon dilatation catheter as defined in claim 5 wherein the combined length of the distal and intermediate segments is about 40 cm.

7. A balloon dilatation catheter as defined in claim 5 further comprising, in combination, a guidewire extending through the guidewire lumen.

8. A catheter for accessing the coronary arteries in a human, the catheter having a proximal end and a distal end and comprising:
   an elongate stiff proximal segment formed of metal;
   a relatively flexible elongate plastic member mounted to the distal end of the proximal segment;
   the proximal segment being smaller in cross-sectional configuration than the plastic member and being substantially stiffer than the plastic member to provide a sufficient column strength for the proximal segment to resist buckling when advanced through the patient's arteries;
   the plastic member having a guidewire lumen formed therethrough the guidewire lumen having a proximal opening in the region of the juncture of the plastic member and the proximal segment and having a distal opening at its distal end, the distal end of the proximal segment being attached to the proximal end of the plastic member in overlapping relation to the proximal end of the guidewire lumen, whereby when a guidewire is contained within the lumen, the catheter will have continuous column support from its proximal end to its distal tip;
   the guidewire lumen extending through the elongate plastic member being open only at said proximal and distal openings, the plastic member completely and continuously circumscribing the guidewire lumen to preclude a guidewire from exiting the guidewire lumen laterally between the proximal and distal openings; and
   an instrumentality carried by the distal end of the plastic member adapted to perform a procedure in a coronary artery.

9. A catheter as defined in claim 8 wherein the instrumentality adapted to perform a procedure in an artery comprises a dilatation balloon and where the proximal segment and the plastic member have an inflation lumen fluidly communicating the interior of the balloon with the proximal end of the catheter.

10. A catheter as defined in claim 9 wherein the plastic segment is about 40 cm long.

11. A catheter as defined in any of claims 8, 9 or 10 further comprising, in combination, a guidewire extending through the guidewire lumen.

12. A catheter as defined in claim 9 wherein the guidewire is about 175 cm long.

13. A catheter as defined in claim 8 wherein the plastic segment is between 35 to 45 cm long.

14. A catheter as defined in claim 13 further comprising, in combination, a guidewire in the guidewire lumen.

15. A method for performing a procedure in a coronary artery comprising:
   providing a catheter for accessing the coronary arteries in a human, the catheter comprising an elongate stiff proximal segment formed of hypotubing; a flexible elongate plastic member mounted to the distal end of the proximal segment, the plastic member having a guidewire lumen formed therethrough, the guidewire lumen having a proximal opening in the region of the juncture of the plastic member and the proximal segment and having a distal opening at its distal end, the distal end of the hypotubing being connected to the plastic member in overlapping relation to the proximal end of the guidewire lumen and the proximal opening thereof, whereby when a guidewire is contained within the lumen, the catheter will have a continuous column support from its proximal end to its distal tip; the proximal segment being of smaller cross-sectional dimensions than the plastic member and being substantially stiffer than the plastic member to provide substantial column strength for the proximal segment to resist buckling when advanced through the patient's arteries; and an instrumentality carried by the distal end of the plastic member adapted to perform a procedure in a coronary; artery;
   percutaneously placing a small diameter steerable guidewire in the patient's arteries and advancing the guidewire into a selected coronary artery;
   percutaneously inserting the catheter into the patient's arterial system over the guidewire;
   advancing the catheter through the patient's arterial system over the guidewire to place the distal end of the catheter in the coronary artery, with the juncture of the plastic portion and proximal portion of the catheters being disposed proximal of the aortic arch;
   whereby the relatively stiff proximal segment of the catheter will remain substantially straight within the descending aorta and the catheter will be supported by the guidewire fully through the aortic arch and into the patient's coronary arteries.

16. A method as defined in claim 15 further comprising:
   performing a catheter exchange including the steps of withdrawing said catheter while holding the guidewire from its proximal end thereby to maintain the position of the guidewire;
   advancing another of said catheters over the guidewire and advancing the catheter along the guidewire to the intended site in the patient's coronary arteries.

17. A method as defined in claim 15 wherein the proximal segment of the catheter is formed from metal.

18. A method as defined in claim 15 wherein said instrumentality comprises a dilatation balloon;
   means extending through the catheter for inflating and deflating the balloon; and
   inflating the balloon within a coronary artery.

19. A readily exchangeable balloon dilatation catheter comprising:
   an elongated, high strength proximal tubular member formed of hypotubing, having proximal and distal ends, and an inner lumen extending therein;
   a flexible distal tubular member secured to the distal end of the high strength proximal tubular member, the tubular member having an inflation lumen extending longitudinally therein with a proximal end in fluid communication with the inner lumen of the high strength proximal tubular member and a distal end with an inflation port therein, the distal tubular member having a guidewire receiving lumen with a first guidewire port in the proximal end thereof and a distal guidewire port in the distal end thereof, the distal end of the proximal tubular member being connected to the distal tubular member in overlapping relation to the proximal end of the guidewire lumen, the proximal guidewire port being spaced longitudinally from the distal port in the distal end a distance sufficient to provide guidewire support along the full length of the flexible distal tubular member; and an inflatable, relatively inelastic balloon on the distal tubular member having a distal end sealingly bonded about the distal end of the distal tubular member and an interior which is in fluid communication with the inflation lumen through the inflation port thereof.

20. A readily exchangeable balloon dilatation catheter comprising:

an elongated, high strength proximal tubular member formed of hypotubing, having proximal and distal ends, and an inner lumen extending therein;

a flexible distal tubular member secured to the distal end of the high strength proximal tubular member, the tubular member having an inflation lumen extending longitudinally therein with a proximal end in fluid communication with the inner lumen of the high strength proximal tubular member and a distal end with an inflation port therein, the distal tubular member having a guidewire receiving lumen with a first guidewire port in the proximal end thereof and a distal guidewire port in the distal end thereof, the distal end of the proximal tubular member being connected to the distal tubular member in overlapping relation to the proximal end of the guidewire lumen, the proximal guidewire port being spaced longitudinally from the distal port in the distal end a distance sufficient so that it extends over the aortic arch of a patient during a balloon dilatation procedure; and an inflatable, relatively inelastic balloon on the distal tubular member having a distal end sealingly bonded about the distal end of the distal tubular member and an interior which is in fluid communication with the inflation lumen through the inflation port thereof.

21. A rapidly exchangeable balloon dilatation catheter for accessing the coronary arteries of a human comprising:

an elongate wire-like shaft having proximal and distal ends and including a proximal tubular member formed from hypotubing, the shaft having sufficient column strength to enable it to be advanced through a patient's vasculature to the coronary arteries, the proximal tubular member having a lumen extending therethrough;

a distal tubular member sufficiently flexible to access the coronary arteries but itself having insufficient column strength for such access without additional support, the distal member being secured to the distal end of and extending distally beyond the distal end of the shaft, the distal member having an inflation lumen extending longitudinally therein and having a proximal end in fluid communication with the lumen of the hypotubing, the inflation lumen being in communication with a balloon inflation port formed in the distal tubular member;

the distal tubular member including a longitudinally extending guidewire lumen receptive to a guidewire and having a distal port and a proximal port, the guidewire lumen extending from the distal region of the shaft to the distal end of the catheter and over a distance sufficient, when a guidewire is position through the guidewire lumen, to provide the flexible distal tubular member with sufficient column strength to access the coronary arteries, the distal end of the proximal tubular member being connected to the distal tubular member in overlapping relation to the proximal end of the guidewire lumen, the guidewire and the shaft together supplying support along the full length of the catheter to enable the catheter to be pushed and advanced to a desired location in the coronary arteries; and an inflatable, relatively inelastic balloon mounted on the distal tubular member having a distal end sealingly attached to the distal end of the distal tubular member and an interior in fluid communication with the inflation lumen through the inflation port.

22. A method for performing a procedure in the coronary arteries in a human comprising:

providing a catheter for accessing the coronary arteries in a human, the catheter having an elongate wire-like shaft having proximal and distal ends and including a proximal tubular member formed from hypotubing, the shaft having sufficient column strength to enable it to be advanced through a patient's vasculature to the coronary arteries, the proximal tubular member having a lumen extending therethrough, a distal tubular member sufficiently flexible to access the coronary arteries but itself having insufficient column strength for such access without additional support, the distal member being secured to the distal end of and extending distally beyond the distal end of the shaft, the distal member having an inflation lumen extending longitudinally therein and having a proximal end in fluid communication with the lumen of the hypotubing, the inflation lumen being in communication with a balloon inflation port formed in the distal tubular member, the distal tubular member including a longitudinally extending guidewire lumen receptive to a guidewire and having a distal port and a proximal port, the distal end of the proximal tubular member being connected to the distal tubular member in overlapping relation to the proximal end of the guidewire lumen;

percutaneously placing a guidewire in the patient's arteries and advancing the guidewire into a selected coronary artery;

percutaneously inserting the catheter into the patient's arterial system over the guidewire;

advancing the catheter through the patient's arterial system over the guidewire to place the distal end of the catheter in the coronary artery;

whereby the guidewire lumen extends from the distal region of the shaft to the distal end of the catheter and over a distance sufficient, when a guidewire is positioned through the guidewire lumen, to provide the flexible distal tubular member with sufficient column strength to access the coronary arteries, the guidewire and the shaft together supplying support along the full length of the catheter to enable the catheter to be pushed and advanced to a desired location in the coronary arteries.

* * * * *